United States Patent [19]

Killeen

[11] Patent Number: 5,026,555

[45] Date of Patent: Jun. 25, 1991

[54] METHOD FOR PREPARING AN ANION EXCHANGE RESIN DELIVERY SYSTEM

[75] Inventor: Michael J. Killeen, Lafayette, N.J.

[73] Assignee: Warner-Lambert Co., Morris Plains, N.J.

[21] Appl. No.: 263,846

[22] Filed: Oct. 28, 1988

[51] Int. Cl.$^5$ .............................................. A61K 47/00
[52] U.S. Cl. ..................................... 424/439; 424/79
[58] Field of Search .................. 424/439, 440, 441, 79

[56] References Cited

U.S. PATENT DOCUMENTS 4,778,676 10/1988 Yang et al. ........................... 424/441
4,818,539 4/1989 Shaw et al. ......................... 424/441

Primary Examiner—Ellis P. Robinson
Assistant Examiner—P. L. Prater
Attorney, Agent, or Firm—Carl W. Battle; Charles A. Gaglia, Jr.

[57] ABSTRACT

A method for preparing an edible anion exchange resin delivery system which comprises the steps of coating granules of resin with lecithin. A gelatin frappe is separately prepared and placed into a mixing chamber. The lecithin-coated resin granules are then added to the chamber and mixed together with the frappe. Flavorings can also be added to the mixture and the final blend is then allowed to set-up in a controlled environment for a predetermined period of time.

13 Claims, 4 Drawing Sheets

METHOD FOR PREPARING AN ANION EXCHANGE RESIN DELIVERY SYSTEM

FIELD OF THE INVENTION

This invention pertains generally to a method for preparing an edible basic anion exchange resin delivery system. More specifically, this invention pertains to a method for blending lecithin-coated edible anion exchange resin granules with a gelatin frappe and selected flavorings. This invention is particularly, but not exclusively, useful for preparing a delivery system which can be ingested by a patient to introduce edible anion exchange resin into the patient's system for reducing the patient's cholesterol level.

BACKGROUND OF THE INVENTION

It is widely known that high levels of cholesterol can create various health complications. For example, high levels of cholesterol have been directly linked with blockages in arteries which restrict and impede blood flow to vital organs in the body. Additionally, cholesterol is known to be present in gallstones, in various cysts and in carcinomatous tissue. For these and other reasons, the reduction of unnecessarily high cholesterol levels is desirable.

Without question, in the vast majority of cases the most effective way to reduce cholesterol levels is with a proper diet. Unfortunately, not everyone is able or willing to discipline themselves to maintain such a diet. Further, it may be that diet alone is ineffective for reducing cholesterol in the system to a desired level. Thus, where high cholesterol levels have been identified as a potential health problem, and dieting is either undesirable or ineffective, various alternatives to the strict diet approach for confronting the problem have been suggested. For example, dietary fibers, such as chitin and chitosan, have been successful in lowering blood cholesterol levels in laboratory animals. These drugs have also had some success in human experiments. Another dietary fiber, cholestyramine an edible anion exchange resin, has been found to be particularly effective for lowering cholesterol levels in humans when ingested in accordance with a prescribed regimen.

Edible anion exchange resins such as cholestyramine, colestipol and the like are chemicals that combine with bile acids and cholesterol in the stomach and intestines. Then, rather than being absorbed into the body's blood system, the bound cholesterol and bound bile acids are excreted and eliminated from the body without effect. Such resins, however, have a very unpleasant taste when ingested alone. Further, ingestible resins have a sand-like constituency which can be difficult to prepare for consumption. Throughout the following discussion, colestipol may be used interchangeably with or instead of cholestyramine.

Presently, in order to make cholestyramine palatable, it is necessary to mix cholestyramine granules With a carrier such as orange juice. This delivery system, however, requires preparation and planning in that the cholestyramine must be stirred up in the juice and ingested before it can settle out. This may require repetitive efforts and can be quite bothersome.

Delivery systems different from orange juice can obviously be proposed. Cholestyramine, however, because of its sand-like constituency, it not an easy material to work with. Indeed, the sand-like characteristic of cholestyramine causes its mixture with certain matrix elements to behave as a Bingham plastic. The result is a composition which is very resistive to mixing or agitation. Nevertheless, the present invention recognizes that cholestyramine can be mixed with a gelatin frappe, in accordance with selected procedures, to produce an acceptable delivery system in spite of any material processing difficulties. In the contemplation of the present invention, this delivery system will resemble the well known and familiar candy bar.

The present invention provides a method for preparing an edible anion exchange resin delivery system which is acceptable for ingestion by a human. In addition, the present invention sets forth a method which makes a cholestyramine delivery system that tastes good and is easy to ingest and which allows edible anion exchange resins to be easily and efficaciously ingested with little, if any, pre-ingestion preparation. A simple cost effective procedure for preparing an edible anion exchange resin delivery system which can be efficaciously followed in spite of the delivery system's tendency to exhibit the characteristics of a Bingham plastic is also described.

Cholestyramine as used herein is representative of the class of compounds known as edible anion exchange resins. This class of compounds is useful in the present invention. Anion exchange resins useful in the present invention include those anion exchange resins having anticholesteremic properties which promote a reduction of cholesterol levels in the blood. Preferred anion exchange resins include cholestyramine, colestipol and anion exchange resins having the imidazolium group as the functional group. Preferred resins of the imidazolium type are described in U.S. Pat. No. 4,557,930 the entire contents of which are hereby incorporated by reference.

SUMMARY OF THE INVENTION

The preferred method for preparing a cholestyramine delivery system comprises the step of coating cholestyramine resin granules with lecithin to disguise the unpleasant taste of the cholestyramine. A gelatin solution is separately prepared and mixed together with selected sweeteners and bulking agents. The lecithin-coated cholestyramine granules are then added to the gelatin frappe and mixed with the frappe until the granules are evenly suspended therein. Flavorings and additional gelling agents can be added to this mixture as desired to enhance consumer acceptance of the delivery system.

The final blend of the cholestyramine delivery system is then placed into a controlled environment where it is allowed to set-up. Preferably, temperature-regulated air-tight containers are used to provide this controlled environment.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED METHOD

Figure 1:
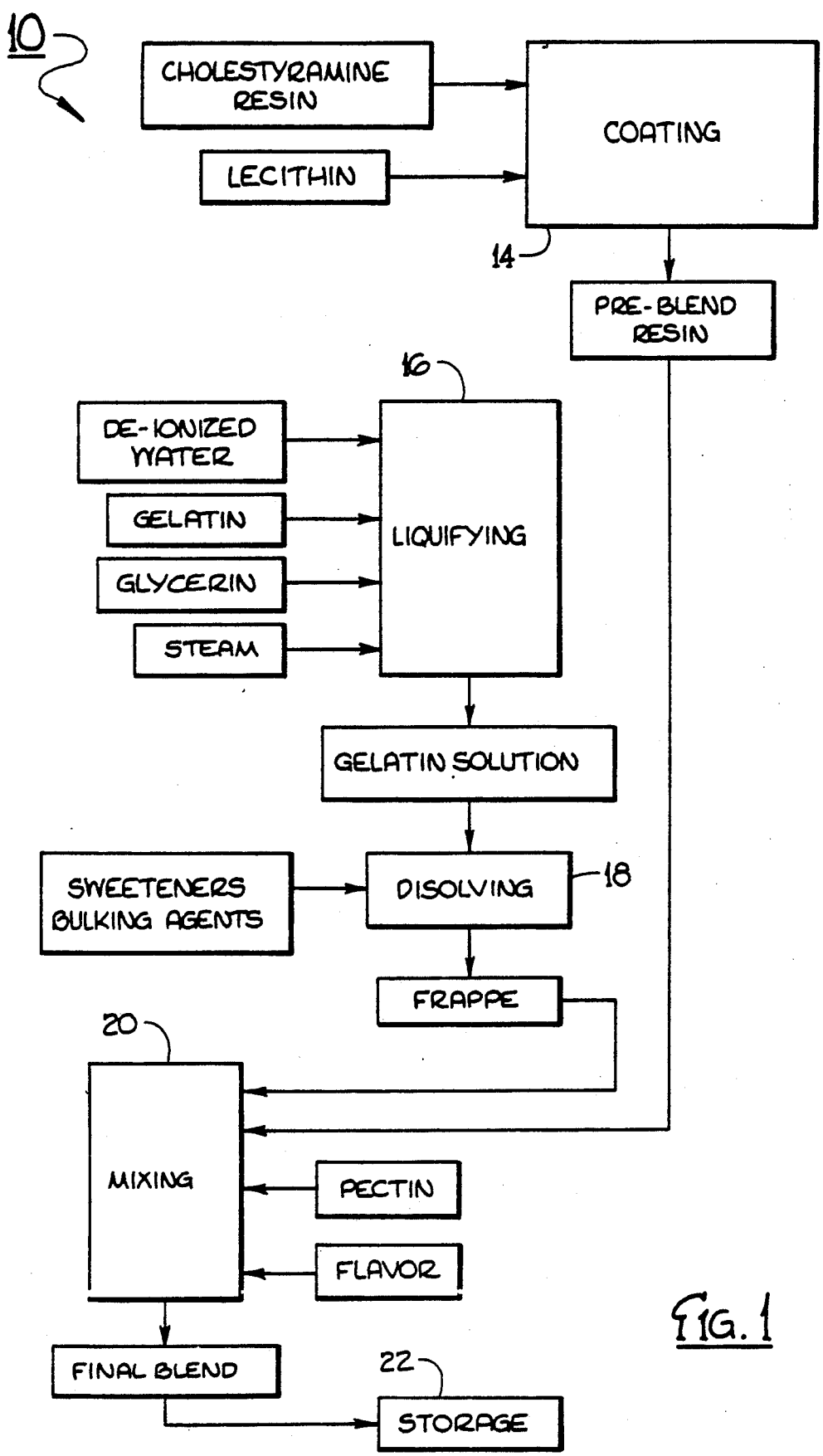
FIG. 1 is a block-diagram of the method used to manufacture a cholestyramine delivery system.

Referring initially to FIG. 1, a procedural block diagram for the method of the present invention is shown and generally designated 10. As a general statement, this method comprises all steps necessary to prepare and mix lecithin-coated cholestyramine granules with a gelatin frappe to create an edible cholestyramine delivery system. Different flavorings and texture modifiers can also be added for enhancing the acceptability of the delivery system. The final blend of these ingredients is then stored under controlled conditions until it can be apportioned and sized into a commercially viable product.

The general procedure for preparing the cholestyramine delivery system in accordance with the present invention is set forth when reading diagram 10 in FIG. 1 from top to bottom. First, it is understood that a Cholestyramine Resin USP is preferably used which is commercially available as granules having a consistency of fine sand. Because cholestyramine has an unpleasant fishy taste, as the first step in the procedure, the cholestyramine granules are preferably coated with an agent such as lecithin which will mask or disguise this unpleasant characteristic of cholestyramine. This part of this procedure is indicated by the functional descriptor shown in box 14. Preferably, lecithin (Alcolec - 495) is used for this purpose. As intended by the present invention, this coating is accomplished by the mechanical and thermal effects caused when a chopper blade is rapidly moved through the material. A complete discussion of the necessary equipment and its use in performing the various steps of this procedure are subsequently set forth. It is sufficient for now to recognize that lecithin-coated cholestyramine granules are prepared as an ingredient which has been designated as pre-blend resin in FIG. 1.

Preferably, in making the pre-blend cholestyramine resin and lecithin are combined in the ratio of five (5) parts cholestyramine for each one (1) part lecithin. Due primarily to the relatively unstable nature of lecithin in the pre-blend resin, the complete process for making the cholestyramine delivery system should be continued and complete as soon as possible. If however, the pre-blend resin cannot be used relatively quickly and some storage is necessary, it should be noted that during storage pre-blend resin should be protected from heat, light and air in order to prevent damage. Importantly, the storage time for pre-blend resin is limited. At room temperature, pre-blend resin has a shelf life of approximately twenty-four (24) hours. This shelf life can be extended to approximately seventy-two (72) hours if the temperature is either lowered to four (4) degrees centigrade or the pre-blend is stored under Nitrogen.

In a separate operation, from that for the preparation of the pre-blend, a gelatin, such as Gelatin USP Granules, is liquified in deionized water as indicated by the functional description shown in box 16. Glycerin, such as Anhydrous USP 99.5%, is then added to the dissolved gelatin. When a Stephan mixer is used for this process, in a manner to be subsequently disclosed, steam is introduced to the mixture to enhance further liquification of the constituents of the mixture which is referred to in FIG. 1 as a gelatin solution. Preferably, the proportional parts of water, gelatin and glycerin in the gelatin solution are respectively in the range of twelve (12) parts, one (1) part and five (5) parts.

As indicated in FIG. 1, sweeteners and bulking agents are dissolved into the gelatin solution as shown by the functional descriptor in Box 18. Preferably, the sweetening and bulking agents are Fructose NF and sorbitol such as Sorbitol Crystalline Gamma Form. During this dissolving step, the mixture is agitated while the gelatin begins to set up. The result is a fluffy textured frappe. Importantly, this frappe must be sufficiently viscous to suspend the pre-blend resin therein and, because the gelatin frappe begins to set-up as it is being prepared, the frappe cannot be stored for any extended period of time. Consequently, it needs to be mixed with the pre-blend resin soon after it has been prepared.

To prepare the final blend, the frappe is added as rapidly as possible to the pre-blend resin and combined therewith. Pectin, such as Type XSS100 (150 Grade), is then added to act as additional structure for the final blend and a selected flavoring is added to enhance the palatability and desirability of the product. Understandably, various flavorings can be used. In this regard, it has been determined that Mocha, Caramel, Pineapple, Strawberry and Raspberry flavorings work well.

Mixing the various ingredients into a final blend, as indicated at box 20 in FIG. 1, has some unique difficulties which arise due to the fact the final blend exhibits the characteristic of a non-newtonian fluid. More specifically, the final blend behaves as a Bingham plastic. Basically, this means that in the range of practical operations, mixing of the final blend must be accomplished at relatively slow mixing speeds in order to avoid the very substantial shear resisting forces which will occur with only sight additional increases in the mixing speed. Unfortunately, even relatively slow mixing speeds may cause the mixing apparatus to break down. This is so because at levels of operable shear stress, the slope o the flow curve (i.e. a change in shear stress per change in shear rate) is very high. Accordingly, the operable range for mixing cholestyramine is effectively confined well below the yield point of the cholestyramine mixture. As will be subsequently discussed, however, selected equipment can be precisely operated to overcome or circumvent these difficulties caused by the adverse physical characteristic of the final blend.

As indicated by the functional descriptor in box 22 of FIG. 1, proper storage is a necessary and final step in the preparation of the cholestyramine delivery system before it is shaped and packaged for commercial purposes. Some storage of the final blend is necessary in order to allow the mixture to set-up to facilitate subsequent handling and extrusion of the end-product. Preferably, storage of the final blend is done in sealable bins or plastic lined drums wherein the final blend can be protected from air and heat. If properly stored, final blend may be kept at least as long as ten (10) days.

The following representative composition is intended to be exemplary only. It is not meant in any way to restrict the effective scope of the invention. All percentages given in the representative composition are with respect to the total weights of the final blend.

| Ingredient Description | Formula % |
| --- | --- |
| Fructose N.F. | 43.76 |

-continued

| Ingredient Description | Formula % |
| --- | --- |
| Sorbitol Crystalline Gamma Form | 12.00 |
| Water, Deionized | 12.00 |
| Gelatin USP Granules | 1.00 |
| Glycerin Anhydrous USP 99.5% | 5.00 |
| Cholestyramine Resin USP | 20.00 |
| Lecithin (Alcolec - 495) | 4.00 |
| Pectin; Type XSS100 (150 Grade) | 1.44 |
| Mocha Flavor, Artificial F-20590 | 0.80 |
| TOTAL | 100.0 |

Figure 2:
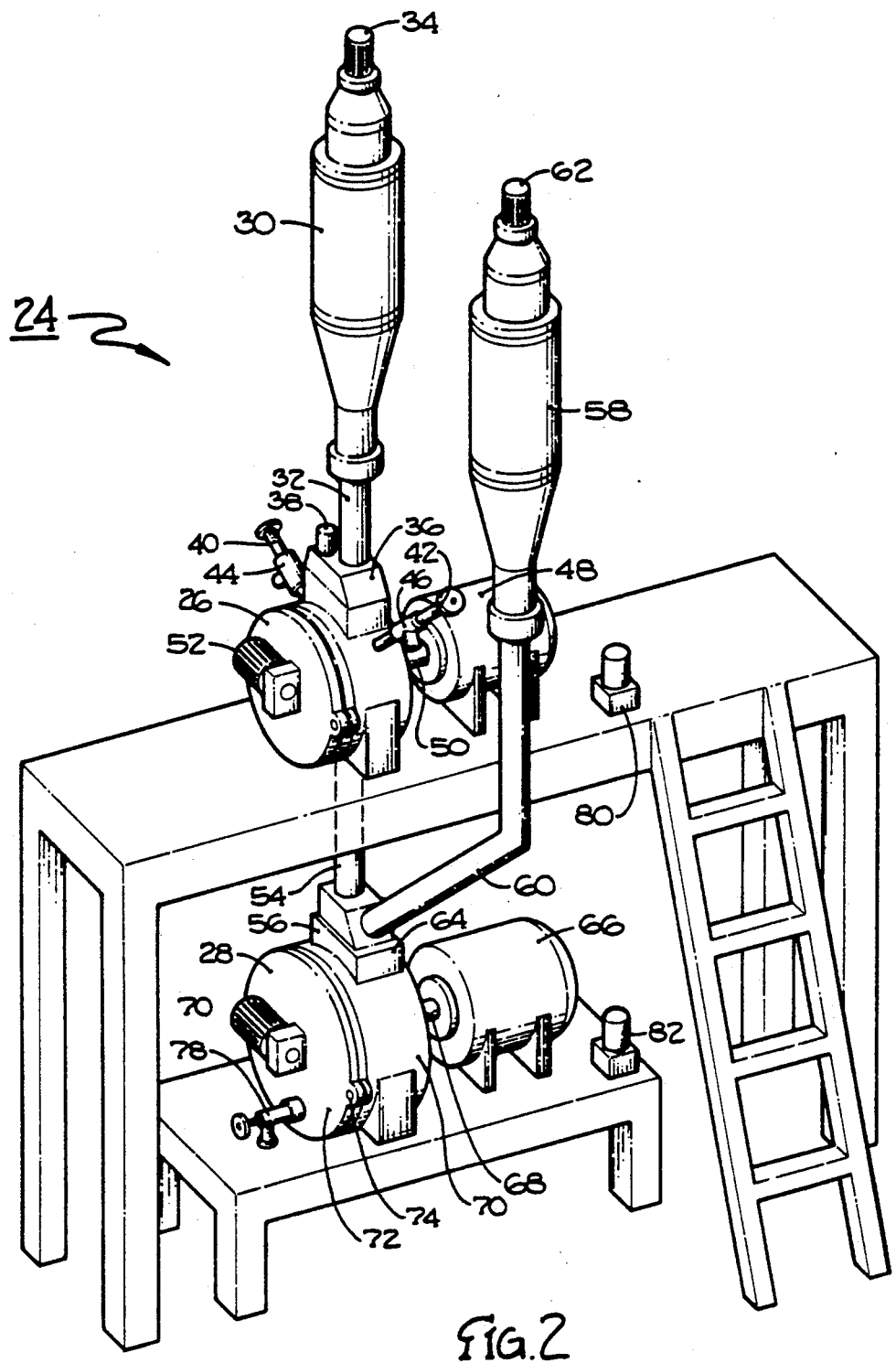
FIG. 2 is a perspective view of two mixers in series used to manufacture the cholestyramine delivery system of the present invention.

Referring now to FIG. 2, an equipment system for preparing the ingredients and mixing the final blend for the cholestyramine delivery system is shown and generally designated 24. Essentially, system 24 comprises a mixer 26 and a mixer 28 which are operatively connected to each other in series. More specifically, mixer 26 is positioned above mixer 28 for a purpose to be subsequently discussed. As shown in FIG. 2, a hopper 30, for holding various ingredients prior to their transfer into mixer 26, is connected to mixer 26 by a connector 32. Hopper 30 may include a stirrer (not shown) which can be activated by motor 34 whenever the ingredients in hopper 30 require agitation.

A manifold 36 is provided to control the flow of material through connector 32 into mixer 26. Likewise, manifold 36 can control the rate at which material is introduced into mixer 26 through inlet 38. Additional access to the interior chamber of mixer 26 can be made through inlets 40 and 42. To enable the controlled entry of fluids through inlets 40 and 42 they are respectively provided with valves 44 and 46.

A motor 48 is provided to rotate a shaft 50. As will be subsequently appreciated, shaft 50 is intended to rotate apparatus (not shown in FIG. 2) for mixing materials introduced into mixer 26. A motor 52 and its associated apparatus (also not shown in FIG. 2) are provided for a similar purpose.

As shown in FIG. 2, mixer 26 is serially connected to mixer 28 by a chute 54. A manifold 56, operatively associated with chute 54, is positioned to control the flow of material from mixer 26 to mixer 28. A hopper 58 is connected directly with mixer 28 by a chute 60. A motor 62 is operatively associated with hopper 60 to activate apparatus (not shown) within hopper 58 if it is necessary for the materials held therein to be agitated.

Thus, it will be appreciated that materials from mixer 26 may be added to mixer 28 via chute 54 and materials from hopper 58 may be added to mixer 28 via chute 60. Also, material may be manually added to mixer 28 through an opening into the mixer 28 which is covered by loading door 64.

A motor 66 is connected to shaft 68 for the consequent rotation of apparatus (not shown in FIG. 2) within mixer 28. The mixer 28, itself, comprises a chamber 70 having a hinged front door 72 which is held in operative association with chamber 70 by a latch 74. A motor 76 is mounted on front door 72 and is operatively connected with apparatus (not shown) for turning or rotating this apparatus within chamber 70. An outlet 78 is also provided which is mounted on front door 72 to allow the removal of material from chamber 70 when front door 72 is closed. Mixer 28 may also be provided with a trap door (not shown) which is on the bottom of mix 28. Preferably, the final blend of cholestyramine material which has been processed by mixer 28 is removed from mixer 28 through this trap door.

Apart from their different inlet and outlet configurations, mixer 26 and mixer 28 are substantially similar in all important operative aspects. Both mixers 26 and 28 each have independent motor-rotated means which can be operated either separately or in concert. Further, mixers 26 and 28 both have chambers with hinged front doors which can be closed and latched during operation, and both have respective remote controls 80 and 82 which facilitate the opening and closing of the various inlets and outlets.

This disclosure so far has impliedly involved a Stephan mixer of the type commercially available as the Stephan Combicut TC/SK model. This mixer is effective for use as both mixer 26 and mixer 28. A more detailed appreciation of this machine can be obtained by reference to FIG. 3.

Figure 3:
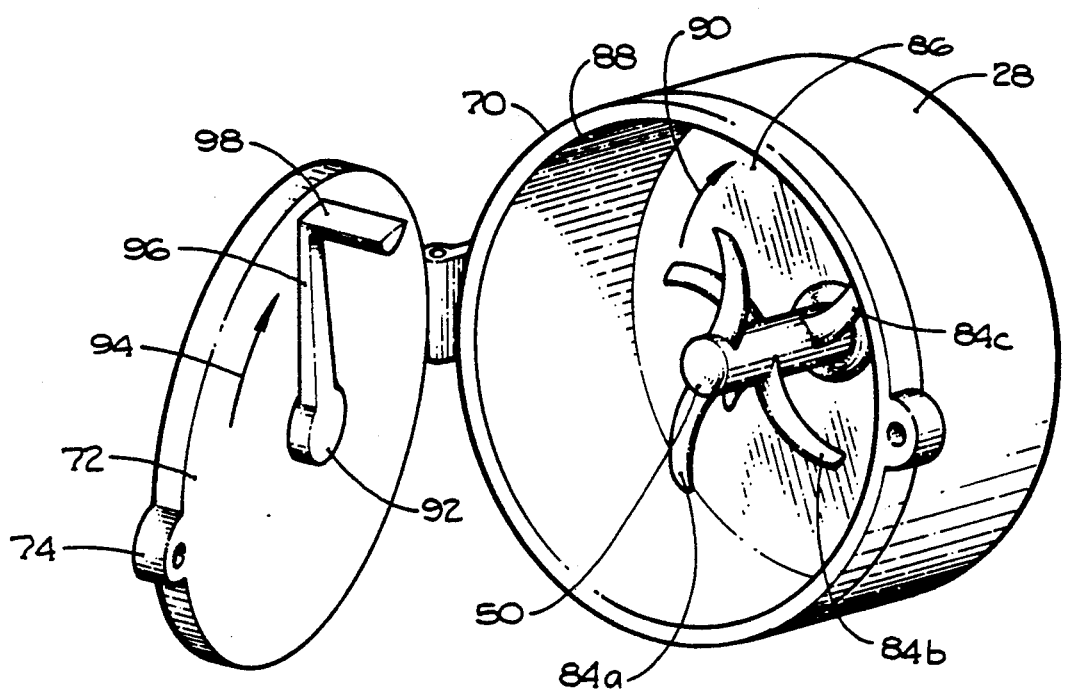
FIG. 3 is a perspective view of the interior of a mixer of the type illustrated in FIG. 2.

In FIG. 3, the mixer 28 is shown with front door 72 opened. This reveals that a plurality of sickle-shaped blades 84a, 84b and 84c are fixedly attached to shaft 50 by any means well known in the art. Also, this shows that chamber 70 is defined by a back wall 86 ad a circular side wall 88 which configure chamber 70 into the shape of a hollow cylindrical bowl. Further, it will be appreciated that shaft 50 eccentrically extends into chamber 70 through back wall 86. Rotation of shaft 50 by motor 48 causes a consequent rotation of blades 84 in the direction of arrow 90.

FIG. 3 also shows that a short shaft 92 is rotatably mounted at the center of front door 72 for rotation by motor 52 in the direction indicated by arrow 94. An arm 96 extends from short shaft 92 substantially as shown and a scrapper 98 is positioned substantially perpendicular to the arm 96.

It can be appreciated by the skilled artisan that when door 72 is closed, scraper 98 is positioned within chamber 70 for movement along the curved surface of side wall 88. Further, it will be appreciated that blades 84a, 84b and 84c are rotated about shaft 50 counter to the rotation of scraper 98. Accordingly, as blades 84 chop or mix any material which is held within chamber 70, scraper 98 will remove any material which sticks or clings to side wall 88 and fold this material back into the center of chamber 70 for further action by blades 84. Recall that motors 66 and 76 can be independently operated. Thus, either scraper 98 or blades 84 can be held stationary while the other is rotated. Also, this arrangement allows the simultaneous operations of blades 84 and scraper 98 at different speeds.

Figure 4:
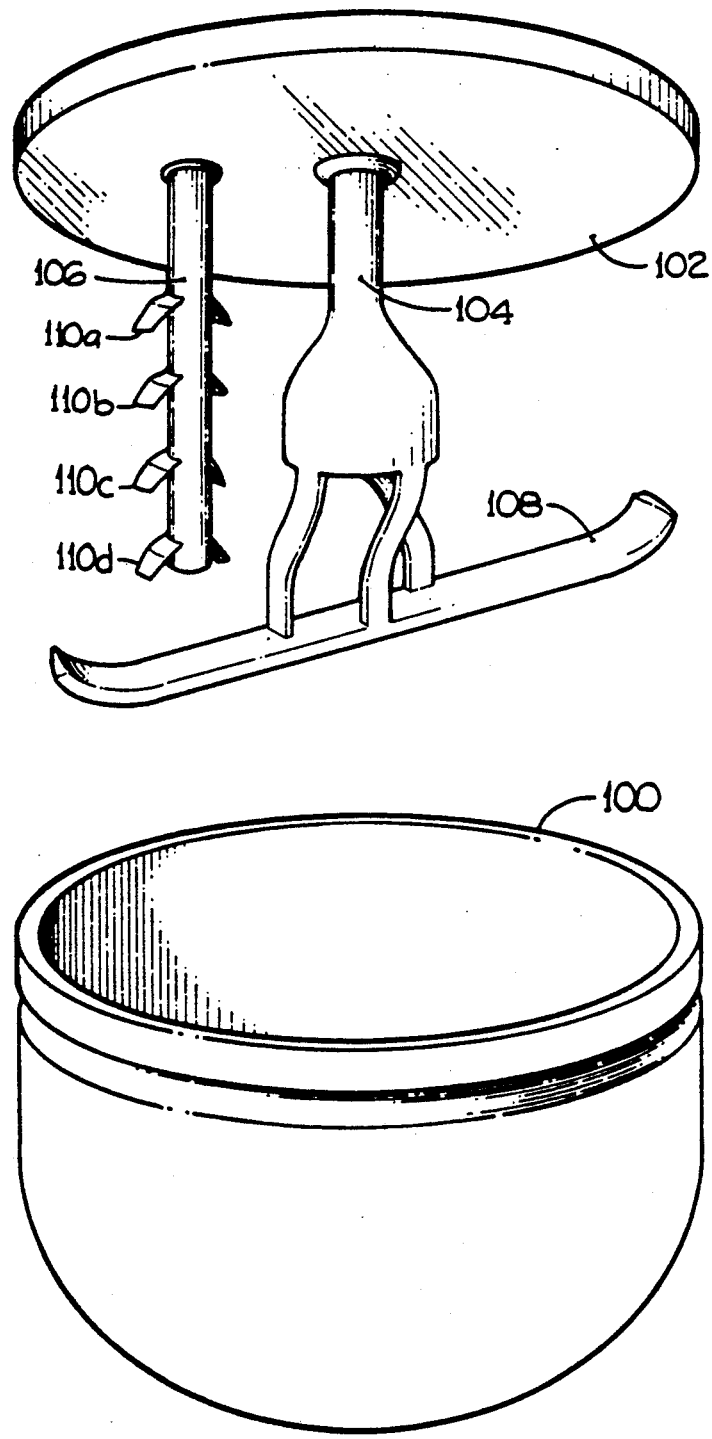
FIG. 4 is a perspective view of the interior of an alternate embodiment of a mixer used to manufacture the cholestyramine delivery system of the present invention.

An alternate embodiment of a mixer for use with the present invention is the GRAL model 75L which is illustrated in FIG. 4. Briefly, the GRAL comprises a round bowl-shaped chamber 100 into which the material to be mixed or processed is placed. A circular top 102 covers chamber 100 and the rotatable shafts 104 and 106 extend through top 102 for positioning within chamber 100. As shown, shaft 104 is concentrically mounted on top 102 while shaft 106 is eccentrically mounted thereon and substantially parallel to shaft 104. FIG. 4 also shows that a blade 108 is attached to shaft 104 and is rotated by shaft 104 within the chamber 100. Similarly, choppers 110a, 110b, 110c and 110d are rotated by shaft 106 in chamber 100. Not shown in FIG. 4 are the motors which rotate shafts 104 and 106. It will be understood by the skilled artisan, however, that such an operation can be accomplished in any of several ways, all known in the art. For purposes of the present invention, it is sufficient to recognize that material within chamber 100 can be effectively agitated by such a device.

The practice of the above-disclosed procedure for making a cholestyramine delivery system, by using the above-disclosed equipment, is best appreciated by cross-referencing FIG. 1 with FIG. 2. With this cross-referencing, it is to be understood that the procedure using the Stephan mixer will be generally discussed. Any procedural differences which are necessitated by use of the GRAL mixer will be disclosed subsequent to the disclosure pertinent to the Stephan.

Typically, the procedure is initiated by making the pre-blend resin. To do this, cholestyramine resin granules are placed into hopper 30 and then transferred from hopper 30 into mixer 26 as desired. Lecithin is then quickly added to the granulated cholestyramine resin in mixer 26 and the ingredients are agitated by the rotation of shaft 50 at approximately 1750 revolutions per minute for one (1) minute. Normally this operation will result in an increase in temperature of the mixture into a range which approximately extends between forty (40) degrees and fifty five (55) degrees centigrade. This temperature rise is sufficient to cause the lecithin to coat the cholestyramine granules. This pre-blend which comprises the lecithin-coated cholestyramine resin granules is then temporarily held within mixer 26.

Room temperature deionized water is introduced into mixer 28. Gelatin and glycerin are then added respectively into mixer 28 and liquified in the deionized water. Steam is then introduced into mixer 28 to further dissolve the constituents and the constituents are mixed together through the concerted action of blades 84 which are rotated by motor 66 at 1750 revolutions per minute and a scrapper 98 which is rotated by motor 76 at 24 revolutions per minute. This mixing requires two (2) minutes. The gelatin solution has thus been prepared and is held within mixer 28 for further use in the procedure.

Once the pre-blend has been prepared and the gelatin solution is being held in mixer 28, the fructose and sorbitol materials are introduced into mixer 28. The gelatin solution, fructose and sorbitol combination is agitated for three (3) minutes within mixer 28 by the operation of motor 66 which rotates blades 84a, 84b and 84c at 1750 revolutions per minute and the concerted operation of motor 76 which rotates scraper 98 at 24 revolutions per minute. The result of this operation is a fluffy textured frappe.

The pre-blend, pectin and selected flavorings are then added to the contents of mixer 28. Specifically, the pre-blend is introduced into mixer 28 through chute 54 and the pectin and flavoring are either added through chute 60 or through manual loading door 64. This entire composition is churned within mixer 28 for one (1) minute by the rotation of blades 84 at 1750 revolutions per minute and the rotation of scraper 98 at 24 revolutions per minute. The product is then removed from mixer 28 and stored for at least twelve (12) hours before further apportionment and sizing into the commercial end-products.

Alternative equipment for manufacturing a cholestyramine delivery system can best be appreciated by cross-referencing FIG. 1 with FIG. 4. With this cross-referencing, it is to be understood that the procedure using the Gral mixer will be generally discussed.

As before, the procedure is initiated by making the pre-blend resin. To do this, cholestyramine resin is placed into chamber 100. A motor (not shown) is started in order to rotate blade 108 at a relatively low speed. Simultaneously with the starting of the rotation of blade 108, lecithin which has been warmed to approximately forty-five (45) degrees centigrade to facilitate pumping is rapidly added into chamber 100. The cholestyramine resin is coated with lecithin by simultaneously rotating blade 108 at approximately 300 revolutions per minute and rotating choppers 110a, 110b, 110c and 110d by a motor (not shown) at approximately 1750 revolutions per minute for ten (10) minutes. Normally this operation will result in an increase in temperature of the mixture into a range which approximately extends between forty-five (45) degrees and fifty-five (55) degrees centigrade. This pre-blend which comprises lecithin-coated cholestyramine resin granules, is then removed from chamber 100 and temporarily stored.

Warm deionized water, i.e. water between seventy-five (75) degrees and eighty (80) degrees centigrade, is introduced into a tank (not shown) which is equipped with an agitator. Gelatin granules are added to the tank and the granules are dissolved by agitating the mixture to create the gelatin solution. After the pre-blend resin has been removed from chamber 100 and chamber 100 has been properly cleaned, fructose and sorbitol are added to chamber 100. The gelatin solution is then mixed with these bulking agents and sweeteners for two and one-half (2½) minutes at 200 revolutions per minute. Chamber 100 is then opened and the wall of chamber 100 and blade 108 are manually scraped to bring together any unmixed solution in the center of chamber 100 for further mixing. The chamber 100 is again closed and the blade 108 is rotated an additional two and one-half (2½) minutes at 200 revolutions per minute.

Pre-blend resin, pectin and selected flavorings are then rapidly added to the frappe in chamber 100 and blade 108 is rotated at a relatively low speed. Choppers 110a, 110b, 110c and 110d are rotated at 1750 revolutions per minute for a short period of time to remove any agglomeration. The chamber 100 is then opened and the wall of chamber 100 and blade 108 are manually scraped to effectuate thorough mixing. The chamber 100 is then closed and blade 108 is rotated an additional short period of time to improve uniformity of the material. The product is then manually removed from chamber 100 and stored for at least twelve (12) hours before further apportionment and sizing into the commercial end-product.

While the particular method for preparing a cholestyramine delivery system as herein shown and disclosed in detail is fully capable of providing the advantages herein before stated, it is to be understood that it is merely illustrative of the presently preferred embodiments of the invention and that no limitations are intended to the details of construction or design herein shown other than as defined in the appended claims.

I claim:

1. A method for preparing an edible anion exchange resin delivery system which comprises the steps of:
   (A) Coating edible anion exchange resin granules having anticholesteremic properties with lecithin by mixing for about one minute said anion exchange resin granules with said lecithin in a hollow, generally cylindrical-shaped mixing chamber having a circular sidewall by rotating at about 1750 revolutions per minute or greater a plurality of blades within said chamber around the longitudinal axis of said chamber and in a plane substantially perpendicular thereto (B) Preparing a gelatin-frappe;

(C) Placing said lecithin-coated anion exchange anion granules and said gelatin-frappe in said mixing chamber;

(D) Moving one or more blade(s) within said mixing chamber for combining said granules with said frappe to create a mixture thereof; and (E) Removing said mixture from said mixing chamber before said gelatin frappe sets up.

2. A method of claim 1 wherein preparation of said gelatin-frappe comprises the steps of:

(A) Mixing gelatin, water and glycerin to form a gelatin solution;

(B) Adding sweeteners and bulking agents to said solution; and (C) Agitating the ingredients to form a fluffy textured frappe.

3. A method for preparing a delivery system as recited in claim 2 further comprising the steps of:

(A) Allowing said mixture to rest for at least twelve hours; and (B) Forming said mixture into bar-shaped portions.

4. A method for preparing a delivery system of claim 1 wherein said gelatin frappe material is prepared in a hollow generally cylindrical-shaped mixing chamber, said chamber having a circular sidewall, by rotating a plurality of blades within said chamber around the longitudinal axis of said chamber and in a plane substantially perpendicular thereto to mix said frappe.

5. A method for preparing a delivery system as recited in claim 1 further comprising the step of aligning the longitudinal axis of said chamber in a substantially horizontal orientation.

6. A method of preparing a delivery system as recited in claim 1 wherein the edible anion exchange resin is selected from the group consisting of cholestyramine, colestipol and anion exchange resins having the imidazolium group as the functional group.

7. A method for preparing a delivery system as recited in claim 1 wherein the edible anion exchange resin is cholestyramine.

8. A method for preparing a delivery system as recited in claim 1 wherein the edible anion exchange resin is colestipol.

9. A method of claim 1 wherein said mixing chamber is substantially as shown in FIG. 3.

10. A method of claim 1 wherein in step (C) said gelatin-frappe is placed in said mixing chamber first and subsequently said lecithin-coated anion exchange resin from step (A) is placed in said mixing chamber.

11. A method of claim 1 wherein in step (D) said granules and said frappe are mixed for about one minute by rotating said blades(s) at about 1750 revolutions per minute or greater.

12. A method of claim 1 further comprising the step of incorporating into said anion exchange resin delivery system one or more flavorings selected from the group consisting of mocha, caramel, pineapple, strawberry and raspberry.

13. A method of claim 1 further comprising the step of moving a scraper blade along said circular sidewall to fold said resin-frappe mixture back into said chamber for contact with said rotating blade(s).

* * * * *